(12) United States Patent
Ray (10) Patent No.: US 9,198,896 B2
(45) Date of Patent: Dec. 1, 2015

(54) IN VIVO ASSESSMENT OF TOXICITY AND PHARMACOKINETICS OF METHYLGLYOXAL

(75) Inventor: Manju Ray, Kolkata (IN)

(73) Assignee: NATIONAL RESEARCH DEVELOPMENT CORPORATION, New Delhi (IN)

( * ) Notice: Subject to any disclaimer, the term of this patent is extended or adjusted under 35 U.S.C. 154(b) by 8 days.

(21) Appl. No.: 12/858,708

(22) Filed: Aug. 18, 2010

(65) Prior Publication Data

US 2011/0118327 A1 May 19, 2011

Related U.S. Application Data

(63) Continuation-in-part of application No. 11/894,736, filed on Aug. 21, 2007, now abandoned.

(60) Provisional application No. 60/838,981, filed on Aug. 21, 2006.

(51) Int. Cl.
| | |
|---|---|
| *A61K 31/4045* | (2006.01) |
| *A61K 31/375* | (2006.01) |
| *A61K 31/121* | (2006.01) |
| *A61K 31/197* | (2006.01) |
| *A61K 31/404* | (2006.01) |

(52) U.S. Cl.
CPC ............ *A61K 31/375* (2013.01); *A61K 31/121* (2013.01); *A61K 31/197* (2013.01); *A61K 31/404* (2013.01); *A61K 31/4045* (2013.01)

(58) Field of Classification Search
None
See application file for complete search history.

(56) References Cited

U.S. PATENT DOCUMENTS

| | | | |
|---|---|---|---|
| 2003/0087951 A1* | 5/2003 | Burman et al. | ............... 514/423 |
| 2006/0045896 A1 | 3/2006 | Morariu | |
| 2008/0188541 A1 | 8/2008 | Ray | |

OTHER PUBLICATIONS

"In vivo assessment of toxicity and pharmacokinetics of methylglyoxal; Augmentation of the curative effect of methylglyoxal on cancer-bearing mice by ascorbic acid and creatine" by Ghosh et al., Toxicol. Appl. Pharmacol. 212, 45-58 (2006).*
"Modulatory Effects of Melatonin and Vitamin E on Doxorubicin-Induced Cardiotoxicity in Ehrlich Ascites Carcinoma-Bearing Mice" by Wahab et al., Tumori 86, 157-62 (2000).*
"Influence of melatonin on proliferation and antioxidant system in Ehrlich ascites carcinoma cells" by El-Missiry et al., Cancer Lett. 151, 119-25 (2000).*
"Combined Treatment with Vitamin B12b and Ascorbic Acid Causes in Vitro DNA Degradation in Tumor Cells" by Medvedev et al., Bull. Exp. Biol. Med. 131, 364-66 (2001).*
"Inhibition of Glycolysis and Mitochondrial Respiration of Ehlich Ascites Carcinoma Cells by Methylglyoxal" by Halder et al., Int. J. Cancer 54, 443-49 (1993).*
"Principles of Cancer Therapy." Cecil's Textbook of Medicine (Twenty-First Edition, vol. 1). W.B. Saunders Company, 2000. pp. 1060-1074.
Ghosh et al. In vivo assessment of toxicity and pharmacokinetics of methylglyoxal augmentation of the curative effect of methylglyoxal on cancer-bearing mice by ascorbic acid and creatine. Toxicology and Applied Pharmacology, 212, (2006), pp. 45-48.
Jung et al. Melatonin in cancer management: progress and promise. Cancer Research, 2006, 66:20.

* cited by examiner

*Primary Examiner* — Theodore R West
(74) *Attorney, Agent, or Firm* — The Webb Law Firm (57) ABSTRACT

A pharmaceutical composition and treatment method to reduce the proliferation of cancerous or tumor cells, in which the combined active agents are methylglyoxal, ascorbic acid, creatine and melatonin.

9 Claims, 5 Drawing Sheets

IN VIVO ASSESSMENT OF TOXICITY AND PHARMACOKINETICS OF METHYLGLYOXAL

CROSS REFERENCE TO RELATED APPLICATION

This patent application is a continuation-in-part application of U.S. patent application Ser. No. 11/894,736, filed Aug. 21, 2007, which claims priority to U.S. Provisional Patent Application No. 60/838,981, filed Aug. 21, 2006, both of which are incorporated herein by reference in their entirety.

BACKGROUND OF THE INVENTION

1. Field of the Invention

This invention relates to the in vivo assessment of toxicity and pharmacokinetics of methylglyoxal and to the curative effect of the pharmaceutical composition on cancer.

2. Description of Related Art

As early as 1913, it was observed that methylglyoxal is converted to d-lactic by a strong and ubiquitous enzyme system. But how methylglyoxal is formed in organisms, and from what precursor(s), was unknown at that time. However, in the 1970s and 1980s, the metabolic pathway for methylglyoxal in different organisms had been established with the isolation, purification and characterization of several enzymes responsible for the formation and breakdown of methylglyoxal. That methylglyoxal is a normal metabolite has been firmly established (for a review, see Ray and Ray, 1998).

The anticancer property of methylglyoxal was also known for a long time. In the early 1960s, Szent-Györgyi et al. proposed that methylglyoxal is a natural growth regulator and can act as an anticancer agent (Együd and Szent-Györgyi, 1966, Együd and Szent-Györgyi, 1968; Szent-Györgyi et al., 1967; Szent-Györgyi, 1979). They also provided strong experimental evidence in support of the hypothesis. When mice were inoculated with ascites sarcoma 180 cells and then treated with methylglyoxal, no tumor developed (Együd and Szent-Györgyi, 1968). At the same time, Apple and Greenberg (1967, 1968) showed remarkable curative effect of methylglyoxal in experiments with mice bearing a wide variety of cancers. Other investigators (Conroy, 1979; Elvin and Slater, 1981) had also observed similar anticancer effect of methylglyoxal.

Együd and Szent-Györgyi (1966) suggested that the anticancer property of methylglyoxal is mediated through the growth inhibitory effect of methylglyoxal, which in turn is due to the inhibition of protein synthesis by methylglyoxal. However, whether there is a qualitative difference in the effect of methylglyoxal between normal and malignant cells had not been systematically investigated. Moreover, very few studies had been done previous to that time with human tissue.

Subsequent studies had indicated that methylglyoxal is tumoricidal. It inhibits both glycolysis and mitochondrial respiration of specifically malignant cells (Ray et al., 1991; Halder et al., 1993; Biswas et al., 1997). With a wide variety of postoperative human tissues and also animal tissues and cells, both normal and malignant, it had been observed that methylglyoxal inhibits mitochondrial respiration (at the level of complex I) and inactivates glyceraldehyde-3-phosphate dehydrogenase of specifically malignant cells (Halder et al., 1993; Ray et al., 1994, 1997a, 1997b; Biswas et al., 1997). These results strongly suggest that these two enzymes are altered specifically in malignant cells.

In contrast to the positive effect of methylglyoxal as referred to above, recent publications on methylglyoxal research overwhelmingly state that methylglyoxal is toxic. Numerous papers have appeared in the literature, which mostly with in vitro studies have shown that methylglyoxal reacts with arginine, lysine and free terminal amino groups in proteins resulting in AGE (advanced glycation end products) formation. The possibilities of many deleterious effects of methylglyoxal in the body have been extrapolated based mostly on these in vitro studies. The notable complications are related to diabetes and cataract formation (Thornalley, 1996; Lee et al., 1999; Morgan et al., 2002; Roberts et al., 2003). Evidence had also been put forward that methylglyoxal is mutagenic (Murata-Kamiya et al., 2000) and induces reactive oxygen species formation (Chan et al., 2005; Chang et al., 2005). Since relatively few in vivo studies with methylglyoxal have been done, it is logical to conceive that many of the purported in vitro toxic effects of methylglyoxal may be overwhelmed by the many countervailing reactions in an intact animal. This consideration especially stems from the reports of significant curative effect of methylglyoxal towards cancer-bearing animals that had been observed and mentioned above. Moreover, in vitro studies with human samples had indicated the inhibitory effect of methylglyoxal on glyceraldehyde-3-phosphate dehydrogenase and mitochondrial complex I of specifically malignant cells. The results of all these studies strongly demand that methylglyoxal alone or in combination with other substances should be tested for the possible efficacy of treating cancer patients. However, it has not been tested until the recent past. On the other hand, methylglyoxal bis-guanylhydrazone, a derivative of methylglyoxal, had undergone clinical trial with limited success (Dunzendorfer et al., 1986; Friedman et al., 1986; Gastaut et al., 1987). A need therefore remains to develop in vivo toxicity assessment techniques to determine the pharmacokinetics of methylglyoxal so that the output of such assessment may be relied on by health care providers to make patient treatment decisions, and a pharmaceutical composition for treating patients for whom methylglyoxal treatment is indicated.

SUMMARY OF THE INVENTION

In order to meet this need, the present invention is a pharmaceutical composition and treatment method to reduce the proliferation of cancerous or tumor cells, in which the combined active agents are methylglyoxal, ascorbic acid, creatine and melatonin.

BRIEF DESCRIPTION OF THE DRAWINGS

FIG. 1 are tissue section photographs which show histological examination of different organs of mice, both untreated (control) and treated orally by methylglyoxal (A and B) Liver, control and treated respectively; magnification 40×. (C and D) Kidney, control and treated respectively; magnification 10×. (E and F) Spleen, control and treated respectively; magnification 40×. (G and H) Duodenum, control and treated respectively; magnification 10×. (I and J) Bone marrow, control and treated respectively; magnification 100×. The stain used for bone marrow was Leishmann for other organs, hematoxylin and eosin.

FIG. 2 is a line graph which shows that blood methylglyoxal concentrations in mice after single oral dose of methylglyoxal. o, ●, ∆, and □ represent 0, 50, 100 and 200 mg of methylglyoxal respectively.

Accordingly, provided herein are compositions for the treatment of Ehrlich's ascites carcinonma (EAC) cancer comprising methylglyoxal, ascorbic acid, creatine and melatonin in combination without toxic effect. The composition may comprise 10 mg-2 g per kg of body weight per day of methylglyoxal in a form that also comprises at least one pharmaceutically acceptable excipient.

The composition may further comprise methylglyoxal and ascorbic acid in a ratio ranging from between 2:5 to 4:1 by weight of the individual components.

The composition may further comprise creatine in an amount of between 100 and 200 mg per kg of body weight per day. This dosage of creatine may be provided in between one and four doses per day.

The composition may comprise melatonin in an amount of between 0.1 mg and 20 mg in an adult per day. The melatonin may be provided in oral dosage form. In further non-limiting embodiments, melatonin is present in an amount of 0.3 mg per day in oral form.

The composition of the present invention may be formulated to be administered orally, subcutaneously, or intravenously.

In a non-limiting embodiment, the composition comprises 20 mg to 1 g of methylglyoxal per kg of body weight per day, 0.5 to 4 g of ascorbic acid administered in three to six doses per day, 100 to 200 mg of creatine per kg of body weight in one to four doses per day, and 0.1 to 20 mg of melatonin per day.

In additional non-limiting embodiments, the composition is provided subcutaneously or intravenously and comprises 0.3 to 1 g of methylglyoxal per kg of body weight per day.

In further non-limiting embodiments, the composition is capable of providing at least 85% inhibition of tumor cell viability in vitro.

In a non-limiting embodiment, the composition is administered orally and comprises 20 mg of methylglyoxal per kg of body weight per day, 50 mg of ascorbic acid in three to six doses per day, 150 mg of creatine per kg of body weight per day in one to four doses per day, and 0.3 mg of melatonin per day.

Also provided herein are methods for treating cancer comprising using a composition comprising methylglyoxal, ascorbic acid, creatine, and melatonin to inhibit cell proliferation. In non-limiting embodiments, the composition is administered without toxic effect on the individual receiving the treatment.

In non-limiting embodiments, the method comprises subcutaneous, oral, or intravenous administration of the composition.

FIG. 3 is a line graph which shows blood methylglyoxal concentrations in mice in repeat oral dose study.

FIG. 4 is a collection of mice photographs that show that effect of methylglyoxal, methylglyoxal plus ascorbic acid and methylglyoxal plus ascorbic acid plus creatine on EAC cell-inoculated mice. Photographs were taken of animals one from each group, EAC cell counts of which are presented in Table 9. Details of inoculation with EAC cells and treatment schedule are described in the legend of Table 9. The photographs were taken on day 18. (A) Normal mice. (B) Control animal (EAC cell-inoculated, without any treatment). (C) Treated with MG 30 mg. (D) Treated with MG 30 mg+AA 50 mg. (E) Treated with MG 30 mg+AA 50 mg+150 mg. The drugs applied were /kg body weight/day.

BRIEF DESCRIPTION OF THE INVENTION

The present study was initiated with the objective to resolve whether methylglyoxal is truly toxic in vivo and to reassess its therapeutic potential. Four species of animals, both rodent and non-rodent, were treated with different doses of methylglyoxal through oral, subcutaneous and intravenous routes. Acute (treatment for only 1 day) toxicity tests had been done with mice and rats. These animals received 2, 1 and 0.3 g of methylglyoxal/kg of body weight in a day through oral, subcutaneous and intravenous routes respectively. Chronic (treatment for around a month) toxicity test had been done with mice, rats, rabbits and dogs. Mice, rats and dogs received 1, 0.3 and 0.1 g of methylglyoxal/kg of body weight in a day through oral, subcutaneous and intravenous routes respectively. Rabbits received 0.55, 0.3 and 0.1 g of methylglyoxal/kg of body weight in a day through oral, subcutaneous and intravenous routes respectively. It had been observed that methylglyoxal had no deleterious effect on the physical and behavioral pattern of the treated animals. Fertility and teratogenicity studies were done with rats that were subjected to chronic toxicity tests. It had been observed that these animals produced healthy litters indicating no damage of the reproductive systems, as well as no deleterious effect on the offspring. Studies on several biochemical and hematological parameters of methylglyoxal-treated rats and dogs and histological studies of several organs of methylglyoxal-treated mice were performed. These studies indicated that methylglyoxal had no apparent deleterious effect on some vital organs of these animals. A detailed pharmacokinetic study was done with mice after oral administration of methylglyoxal. The effect of methylglyoxal alone and in combination with creatine and ascorbic acid on cancer-bearing animals had been investigated by measuring the increase in life span and tumor cell growth inhibition. The results indicated that the anticancer effect of methylglyoxal was significantly augmented by ascorbic acid and further augmented by ascorbic acid and creatine. Nearly 80% of the animals treated with methylglyoxal, plus ascorbic acid, plus creatine, were completely cured and devoid of any malignant cells within the peritoneal cavity.

Metabolite Estimation and Enzyme Assay

Hemoglobin was estimated by reacting the blood sample with Drabkin's reagent to convert it to cyanmethemoglobin and measuring the absorbance at 540 nm. Urea was estimated by reacting it with hot acidic diacetylmonoxime in the presence of semicarbarzide and measuring the rose-purple color at 525 nm. Glucose was estimated by glucose oxidase method in the presence of peroxidase and measuring the absorbance of the colored complex of hydroxybenzoate and 4-aminophenazone at 510 nm. Creatinine was measured by reacting it with alkaline picrate and measuring the absorbance of the red-colored complex at 520 nm. Alkaline phosphatase was assayed by its ability to convert phenyl phosphate to inorganic phosphate and phenol. The later reacts with 4-aminoantipyrine to form an orange-red-colored complex, which was measured at 510 nm. Aspartate transaminase was measured by reacting the reaction product oxaloacetate (from the substrate 1-aspartic acid) with 2,4-dinitrophenyl hydrazine. The hydrazone thus formed gives a characteristic brown color when placed in an alkaline medium and was measured at 505 nm. Alanine transaminase was assayed similarly by 2,4-dinitrophenylhydrazine-alkali color reaction; the substrate and products are 1-alanine and pyruvate respectively.

Creatine kinase was assayed by monitoring the formation of ultimate reaction product NADPH from creatine phosphate and ADP in the presence of glucose, hexokinase, glucose 6-phosphate dehydrogenase and NADP. The reaction was monitored at 340 nm. The isozyme creatine kinase MB was assayed in a similar fashion but in the presence of the antibody to creatine kinase-M monomer.

Methylglyoxal Estimation

Methylglyoxal was estimated by derivatization of methylglyoxal with 1,2-diaminobenzene to produce 2-methylquinoxaline according to the method of Cordeiro and Freire (1996) with some modifications.

Whole blood from either rat or mice was taken by heart puncture. To 1 ml of blood sample, 1 ml of distilled water was added and mixed thoroughly and then treated with 50 µl of 70% ice-cold perchloric acid and kept at room temperature for 30 min. It was then centrifuged at 8000×g for 20 min at 4° C. After rejecting the precipitate, the supernatant was brought to pH 7.0 by dropwise addition of saturated potassium carbonate solution. After 10 min, it was centrifuged at 8000×g for 10 min at 4° C. To 1 ml of the resulting supernatant was added 200 µl of 5 M perchloric acid, 500 µl of diaminobenzene in water, and the volume was made up to 2 ml with water. It was scanned in a spectrophotometer in wavelengths 200-400 nm. Maximum absorbance was observed in wavelength of 334 nm.

A standard solution of methylglyoxal instead of blood treated under identical conditions was scanned as above. The value at a particular concentration of methylglyoxal was used to calculate the amount of methylglyoxal present in the blood. The authenticity of the method was confirmed further in blood sample by utilizing methylglyoxal in presence of glyoxalase I and GSH (Cooper, 1975), where no detectable 2-methylquinoxaline was formed (details not presented). The lowest amount of methylglyoxal that could be detected in our experimental set up was 1 nmol, and the recovery of methylglyoxal from test samples was approximately 95%.

For all toxicity and treatment studies, the amount of methylglyoxal applied was per kg body weight of the animal.

Acute toxicity study: All the animals received methylglyoxal in two divided doses for only 1 day. Three modes of treatment were used: a) oral, through gastric cannula; b) subcutaneous and c) intravenous, through tail vein. For oral treatment, methylglyoxal was diluted in distilled water, and each mice received 0.35-0.5 ml in a single dose. For subcutaneous and intravenous injections, methylglyoxal was diluted in normal saline. Moreover, for intravenous treatment, methylglyoxal solution was passed through a membrane filter of 0.2-µm pore size. For subcutaneous and intravenous injections, 0.25 ml or 0.15 ml of the solution was injected per dose respectively. For test with mice, the animals were divided in groups each containing 6 animals either male or female weighing 18-20 g. For rats, the animals were divided in groups each containing 5 animals either male or female weighing 80-100 g. The control group in each mode of treatment received either water or normal saline.

Long-term (chronic) toxicity study: Mode of treatment and dilution by either water or normal saline were identical to acute toxicity study. Chronic toxicity study was made with four species of animals: mice, rat, rabbit and dog.

Mice. For experiment with these animals, 4 batches of mice were used per mode of treatment. Each batch contained 6 animals either male or female weighing 18-25 g. All the animals received methylglyoxal in two divided doses per day for a total period of 6 weeks; for oral and subcutaneous studies, 6 days per week, for intravenous, 4 days per week due to swelling of tail and adjoining areas. For oral, subcutaneous and intravenous administrations, each animal received 0.7, 0.2 and 0.25 ml per dose respectively. In all the cases, control group received water or normal saline in respective manner.

Histological studies were done with mice, which had received methylglyoxal orally once a day for 10 weeks, 7 days per week. After end of the treatment, the mice were killed, and several organs were excised and processed for histological studies. Bone marrow cells were taken from the marrow cavity of the femur bone.

Rats. For experiment with these animals, 4 batches of rats were used per mode of treatment. Each batch contained 5 rats either male or female weighing 75-80 g per animal. For oral treatment, each rat received 1.5 ml of methylglyoxal solution once a day for 6 weeks, 6 days per week. For subcutaneous treatment, each rat received 0.9 ml of methylglyoxal solution once a day for 4 days per week for 4 weeks. Then, the rats were injected for 3 cycles; one cycle consisted of injections for two consecutive days followed by a rest of 1 day. In intravenous treatment, each rat received 0.5 ml of methylglyoxal per dose, once a day for 6 weeks, 6 days per week.

Rabbits. For experiments with rabbits, two groups were used per mode of treatment. Each group in each mode of treatment consists of 4 animals, either male or female.

However, each animal was placed in a separate cage. For oral treatment, each rabbit received 12-15 ml of methylglyoxal solution once a day for 6 weeks, 6 days per week.

For subcutaneous treatment, each animal received 2-2.5 ml of methylglyoxal once a day for 6 weeks, 4 days per week. For intravenous treatment, each rabbit received 1.4-1.6 ml once a day for 3 weeks, 4 days per week. Then, the animals received injections for 2 consecutive days followed by a rest of 1 day for total period of 15 days.

Long-term toxicity test with non-rodents (dog and bitch). Total of 6 animals (4 dogs and 2 bitches) were used for this experiment. The animals were 3-4 months old. Three different modes of treatment were used; two animals received the formulation orally, the other two by intravenous injection and the other two by subcutaneous injection. The total period of treatment was for 4 weeks (5 days per week). For oral treatment, the animals were fed 10 ml solution of methylglyoxal once a day. For subcutaneous and intravenous treatments, the animals were injected 1.5-2.0 ml of methylglyoxal solution once a day.

Pharmacokinetic Studies:

Single dose study. In single dose study, a batch of 52 mice received methylglyoxal dissolved in water as a single oral dose of either 0 or 50 or 100 or 200 mg/kg of body weight. For methylglyoxal estimation, blood samples were collected by heart puncture, at 0 h (predose) and at intervals of 1 h up to 6 h and then at an interval of 2 h up to 12 h. Two animals were sacrificed for each dose or no dose, and the blood was pooled, and methylglyoxal was estimated. The entire set of above-mentioned experiment was repeated 6 times. Different pharmacokinetic parameters were determined with a one-compartment model with lag time and first order absorption and elimination. Data from single dose experiments were used to set dose for repeat dose experiments (Benet et al., 1996).

We had observed that the concentrations of methylglyoxal in both plasma and whole blood were almost identical in mice. These mice were both untreated and orally treated with methylglyoxal. So, in all our experiments, we measured the level of methylglyoxal in whole blood.

Repeat dose study: For this experiment, 46 mice in each group received orally 100 mg of methylglyoxal per kg of body weight/day in two divided doses (8 am and 8 pm). At day 0, at 10 am, besides 46 mice, 2 mice that did not receive any methylglyoxal were sacrificed and blood was collected by heart puncture, pooled and methylglyoxal was estimated.

From 46 mice that had started orally receiving methylglyoxal, two mice on each day were sacrificed and methylglyoxal estimated in a similar fashion. The administration of methylglyoxal and sacrifice of animals for methylglyoxal estimation continued on days 1-9 (each day) and on days 12, 15, 19, 22, 25, 28, 29 and 30. After that, methylglyoxal administration was discontinued, but two animals from the remaining animals were sacrificed on each day for methylglyoxal estimation (days 31-36).

Table 1 presents a summary protocol of mode and dose of treatment of methylglyoxal for different studies. It appears that there are some variations in the doses applied to different animals through different routes for different studies. But, in all the cases, the doses that were administered were significantly higher than the intended dose for treatment that had been worked out from the previous works of Együd and Szent-Györgyi (1968) and Apple and Greenberg (1968) and also the study presented in this paper.

Biochemical Analyses of Blood:

Rats: One male and one female from each group (i.e., oral, intravenous and subcutaneous and control) on which long term toxicity tests were performed were chosen at random 1 week after completion of the treatment, and blood was extracted, and 2.5-3.0 ml was pooled from each group. After coagulation, the sera was separated by centrifugation at 2000 rpm for 5 min. Hemoglobin was also measured from a small sample of uncoagulated blood.

Dogs. For biochemical analysis, blood samples from each individual animal were collected and processed similarly to that of rats. The samples were collected just before the treatment commenced, in mid-phase of the treatment and 7 days after completion of the treatment. The samples were analyzed for the activities of several enzymes and metabolite contents as per the methods described in the respective assay kit and are briefly mentioned before. Hemoglobin estimation and cell count were done with an uncoagulated sample.

In Vivo Testing of the Efficacy of Methylglyoxal, Ascorbic Acid and Creatine

Increase in life span study. For increase in life span study (ILS), testing was evaluated by calculating the median survival time (MST) of the treated (T) and control (C) groups and expressed as ILS value $[(T/C-1) \times 100]$. The ILS value of >25 is considered for significant activity in these tumors (Geran et al., 1972; Sanyal et al., 1993).

TABLE 1

A summary protocol of mode and dose of treatment of methylglyoxal for different studies

| Animal and different studies | Mode and dose (in gm/Kg of body weight) of treatment | | |
|---|---|---|---|
| | Oral | Subcutaneous | Intravenous |
| Mouse | | | |
| Single for toxicity study ($n^a$ = 6 × 8) | 2 | 1 | 0.3 |
| Single for pharmacokinetic study (n = 52 × 6) | 0.2 | — | — |
| Multiple for toxicity study (n = 6 × 4) | 1 | 0.3 | 0.1 |
| Multiple for pharmacokinetic study (n = 46 × 3) | 0.1 | — | — |
| Multiple for histological study (n = 20 × 2) | 0.5 | — | — |
| Rat | | | |
| Single for toxicity study (n = 5 × 4) | 2 | 1 | 0.3 |
| Multiple for toxicity study (n = 5 × 4) | 1 | 0.3 | 0.1 |
| Multiple for biochemical study Rabbit | 1 | — | — |
| Multiple for toxicity study (n = 4 × 2) Dog and bitch | 0.55 | 0.3 | 0.1 |
| Multiple (n = 6 × 1) | 1 | 0.3 | 0.1 |

Duration of the treatment is described in the text.
$^a$n = number of animals in each group × number of groups.

Increase in body weight: For this experiment, mice were weighed periodically during and after the therapy. The results are expressed as percentage increase in the body weight using the following relationship: percent increase equals $$= \frac{\text{average increase in body weight}}{\text{average initial body weight}} \times 100$$

Tumor growth inhibition study: For this study, the total number of EAC cells was counted. The ascites fluid containing cells were quantitatively removed from peritoneal cavity of two mice for a particular drug combination. The cavity was further washed twice with a fixed volume of 0.9% NaCl. The washing and the ascites fluid containing the cells were pooled and centrifuged at 2000×g for 5 min. The packed cell volumes were noted. A fixed amount of aliquot from the packed cells was appropriately diluted, and the number of cells was counted in a hemocytometer. Averages ($X^- \pm$SEM) were made of these two parameters, and percentage inhibitions $[(1-T/C) \times 100]$ were calculated for each dose of different test combinations.

Statistical analysis: Values were recorded as mean±SEM. Experimental results were analyzed by Student's t test. P<0.05 was considered as the level of significance for values obtained for treated compound to control.

Toxicity Study in Animals:

Acute Toxicity Study

Acute toxicity study was done with two species of animals, mice and rat. The maximum dose of methylglyoxal for each mouse was for oral 2 g, for subcutaneous 1 g and for intravenous 0.3 g.

TABLE 2

Long-term (chronic) toxicity in animals: measurement of body weight

| | Weight of animals* | | | | | |
|---|---|---|---|---|---|---|
| | Oral | | Subcutaneous | | Intravenous | |
| Animal | Control | Treated | Control | Treated | Control | Treated |
| Mice | | | | | | |
| Day 1 | 21.16 ± 1.06 | 20.6 ± 1.1 | 18.16 ± 1.34 | 22.16 ± 0.68 | 23.16 ± 3.2 | 23.3 ± 2.13 |
| Day 90 | 23.6 ± 0.74 | 22.3 ± 1.79 | 18.8 ± 0.68 | 22.87 ± 0.63 | 25.4 ± 2.32 | 25.3 ± 0.74 |
| Rat | | | | | | |
| Day 1 | 78.6 ± 2.15 | 79.4 ± 0.48 | 78.4 ± 2.4 | 79.6 ± 2.05 | 79.5 ± 2.29 | 79.1 ± 1.34 |
| Day 60 | 80.3 ± 1.7 | 81.9 ± 0.89 | 81.2 ± 2.05 | 80 ± 1.26 | 82.3 ± 1.59 | 82.9 ± 1.4 |
| Rabbit | | | | | | |
| Day 1 | 1.4 ± 0.07 | 1.48 ± 0.05 | 1.12 ± 0.08 | 1012 ± 0.08 | 1.5 ± 0.09 | 1.45 ± 0.08 |
| Day 60 | 1.57 ± 0.08 | 1.61 ± 0.05 | 1.3 ± 0.07 | 1.32 ± 0.04 | 1.61 ± 0.08 | 1.55 ± 0.09 |

Amount of methylglyoxal received by each animal: mouse and rat—1 gm (oral), 0.3 gm (subcutaneous) and 0.1 gm (intravenous); rabbit—0.55 gm (oral), 0.3 gm (subcutaneous) and 0.1 gm (intravenous). Total number of animals in each group including control and different modes of treatment: 6 (mice), 5 (rats) and 4 (rabbits). Each set of experiment was repeated 4 times for mice and rats and for rabbits 2 times respectively. For each mode of treatment a similar study with lesser amount of methylglyoxal was done for mice and rats and similar results were obtained. In Table 3, αWeight of animals for mice and rats in gm and for rabbit in Kg.

Acute toxicity study with rat was done in a similar fashion, and similar results were obtained (details of the results are not presented).

Long-term (multiple dose) toxicity study: Long-term toxicity study was done with four species of animals: mice, rats, rabbits and dogs. Mortality, general physical and behavioral conditions and changes of body weight if any were observed for the four different species of animals. Besides observing these parameters, biochemical tests were also performed in blood samples of dog and rat. Fertility and teratogenicity studies were performed with rats and mice. Histological stud-

TABLE 3

Biochemical tests of blood/sera of rats

| | Hb, metabolite content and marker enzyme activities | | | |
|---|---|---|---|---|
| Test | Control | Oral | Intravenous | Subcutaneous |
| Hb (gm/dl) | 10.65 ± 0.85 | 10.4 ± 0.3 | 10.2 ± 0.8 | 10.35 ± 0.35 |
| Serum glucose (mg/dl) | 115 ± 5 | 109 ± 6 | 102 ± 10 | 122 ± 3 |
| Serum Urea (mg/dl) | 25.4 ± 1.8 | 24.3 ± 1.9 | 26.3 ± 2.1 | 23.5 ± 1.3 |
| Serum creatinine (mg/dl) | 0.89 ± 0.15 | 0.82 ± 0.03 | 0.90 ± 0.02 | 0.85 ± 0.03 |
| Serum aspartate transaminase (units/ml) | 155 ± 6.5 | 132 ± 3 | 125 ± 5 | 141 ± 7 |
| Serum alanine transaminase (units/ml) | 32 ± 2.4 | 24 ± 2.5 | 28 ± 1.6 | 28 ± 2.8 |
| Serum alkaline phosphatase (KA units) | 42.6 ± 1.2 | 39.3 ± 1.6 | 41.6 ± 1.2 | 45.3 ± 1.8 |
| Creatine kinase (units/ml) | 0.46 ± 0.03 | 0.37 ± 0.05 | 0.36 ± 0.04 | N.D. |
| Creatine kinase-MB (units/ml) | 0.22 ± 0.03 | 0.16 ± 0.03 | 0.18 ± 0.01 | N.D. |

All the animals were observed up to 90 days. No death was observed. All the animals remained healthy, no weight loss and behavioral change were observed. No external toxic symptoms were noted in animals in general appearance and in respect of skin and hair texture and in behavioral pattern in respect of food and water intake and activity. No other abnormalities were found. We could not determine the LD50 because the abovementioned high dose of treatment has no apparent effect on the animals.

ies were done with several organs of rat subjected to methylglyoxal treatment and compared with that of the untreated animals.

Long-term toxicity (multiple dose) test with mice: All the animals were observed up to 90 days after completion of the treatment and were found to remain healthy. No death and toxic effect (physical and behavioral) were observed during the observation period. However, for subcutaneous treatment, swelling and damage of hair at the point of injection were noted for control and treatment groups.

TABLE 4

Effect of methylglyoxal treatment on the level of several marker enzymes and metabolites of sera and on cell population of blood of dog and bitch.

| | Activities of enzymes, metabolite concentration and blood cells | | | | | | | | |
|---|---|---|---|---|---|---|---|---|---|
| | Before treatment | | | Mid-phase treatment | | | After treatment | | |
| Test | A | B | C | A | B | C | A | B | C |
| Serum glucose (mg/dl) | 99 | 81 | 87 | 102 | 96 | 96 | 85 | 75 | 82 |
| Serum urea (mg/dl) | 14 | 10 | 12 | 14 | 17 | 14 | 16 | 17 | 17 |
| Serum alanine transferase (IU/L) | 16 | 42 | 16 | 28 | 32 | 20 | 32 | 30 | 16 |
| Serum aspartate transferase (IU/L) | 14 | 29 | 22 | 20 | 19 | 14 | 22 | 23 | 21 |
| Serum Alkaline phosphatase (IU/L) | 192 | 269 | 317 | 442 | 190 | 379 | 185 | 179 | 193 |
| Haemoglobin (gm/c.mm) | 7.3 | 9.2 | 9.5 | 9.2 | 9.5 | 10.0 | 8.4 | 6.6 | 8.4 |
| R.B.C. (per c.mm) | n.d. | n.d. | n.d. | 3,50,000 | 3,550,000 | 3,600,000 | 3,40,000 | 2,800,000 | 3,420,000 |
| W.B.C. (per c.mm) | n.d. | n.d. | n.d. | 6,700 | 9,700 | 7,800 | 7,800 | 11,400 | 9,400 |
| Neutrophils (%) | n.d. | n.d. | n.d. | 50 | 58 | 53 | 69 | 49 | 67 |
| Lymphocytes (%) | n.d. | n.d. | n.d. | 45 | 30 | 44 | 26 | 44 | 27 |
| Monocytes (%) | n.d. | n.d. | n.d. | 3 | 2 | 2 | 2 | 3 | 2 |
| Eosinophils (%) | n.d. | n.d. | n.d. | 2 | 10 | 1 | 3 | 4 | 4 |
| Basophils (%) | n.d. | n.d. | n.d. | 0 | 0 | 0 | 0 | 0 | 0 |
| | | | | Mild hypochromia. No abnormal cells. | | | Mild hypochromia. No abnormal cells. | | |
| Weight (in kg) | 3 | 4.5 | 2.5 | n.d. | n.d. | n.d. | 4.5 | 6 | 3.8 |

(A—dog, B—bitch, C—dog) n.d. : not determined.

Histological studies with mice: Histological studies were done with several organs of mice, and the results are presented in FIG. 1. These mice received methylglyoxal orally once a day for 10 weeks, 7 days per week. It appears from the figure that none of the organs tested by histological examination had any adverse effect on oral treatment of methylglyoxal at the particular dose level.

Long-term toxicity (multiple dose) tests with rats: All the animals except those used for biochemical studies (see below) were observed up to 90 days after completion of the treatment and were found to remain healthy. No toxic effect on physical condition and behavioral pattern such as hair texture, food intake etc. and death were observed. However, the subcutaneous injections appeared to be painful for both treated and control groups. The pain appeared to persist for several minutes after injection. In the animals, which received intravenous injections, swelling appeared in the tail and adjoining regions from 3rd week of the treatment. The swelling remained up to about 10 days from end of the treatment. Details are described in the Tables.

Long-term toxicity studies with rabbits and dogs: We also investigated the long-term effect of methylglyoxal treatment of two other species, rabbit and dog. We observed general physical conditions and behavioral pattern of these treated animals with that of the control animals. Similar to the findings of long-term tests on mice and rats, the treated animal (both rabbit and dog) showed no abnormalities in comparison to the control group of animals. We also measured the body weights of the animals. Table 2 shows the body weight of rabbit up to 60 days of observation period. Besides, we also measured several marker enzymes and metabolites in the blood and sera of dog (see below).

Reproductive and teratogenic studies on rats: Because our formulation is intended basically for the treatment of cancer patients, in our opinion, reproductive study is not much relevant. However, in the course of toxicity studies with mice and rats, we kept some male and female animals in a single cage. Some of the female animals after completion of the treatment during the observation period gave birth to healthy litters. So, we tested whether methylglyoxal had any adverse effect on the fertility and teratogenicity.

Fertility: As methylglyoxal had been found to have no adverse effect, we performed fertility tests. For this, 4 female and 1 male were kept together, and 3 such groups were given the formulation orally. Similarly, 3 groups received the formulation as intravenous injections. The dose and treatment schedules were similar to that for the chronic toxicity test. Each female animal was pregnant and on an average gave birth to 5 healthy litters. Neither deformation of organs nor any other abnormalities were observed among the litters.

Teratogenicity: For this test, mating was performed between mice as mentioned above in the case of fertility studies. However, the female animals did not receive any treatment until they were pregnant. But, as soon as they conceived, as indicated by vaginal plug formation, the treatment (oral and intravenous) started and continued for 3 weeks in a similar fashion for chronic toxicity studies. In this experiment also, the female mice gave birth to healthy litters. These litters also grew up healthy with no signs of abnormality. Healthy litters were born again when mating was performed among these animals.

TABLE 5

Pharmacokinetic parameters of methylglyoxal in mice after a single oral dose of methylglyoxal1, 2.

| Dose (mg/kg) | Lag time (min) | $C^3_{max}$ (nmol/ml) | $t_{max}$ (h) | $k_a$ ($h^{-1}$) | V (L/kg) | k ($h^{-1}$) | $t_{1/2}$ (h) | CL (L/h.kg) |
|---|---|---|---|---|---|---|---|---|
| 50 | ≈55 | 13.9 ± 2.85 | ≈4 | 0.277 | 23.31 | 0.33 | 2.1 | 7.69 |
| 100 | ≈50 | 18.7 ± 3.62 | ≈4 | 0.223 | 41.84 | 0.198 | 3.5 | 8.28 |
| 200 | ≈50 | 19.5 ± 3.36 | ≈4 | 0.216 | 80.97 | 0.192 | 3.6 | 15.54 |

1 Values are means.
2. Two mice were used in each dose level.
3. Abbreviations: Cmax—maximum blood concentration, tmax—time to Cmax, ka—apparent absorption rate constant, V—apparent volume of distribution, CL—apparent total body clearance, k—elimination rate constant, t½—elimination half-life.

Table 5 shows the effect on several marker enzymes and metabolites of blood/sera of rats and dogs, which were subjected to long-term toxicity tests.

As mentioned above, we had observed in acute toxicity studies with mice and rats and in chronic toxicity studies with mice, rats, rabbits and dogs that there was no apparent toxic effect of methylglyoxal in physical condition and behavioral pattern of all the animals. No death was observed among the animals, and they remained perfectly healthy. So, we investigated whether, similar to the absence of any apparent external toxic effect, the biochemical functions of some vital organs of the animals remained unchanged. The results for the biochemical studies with rats and dogs are presented in Tables 3 and 4 respectively. It appears from Table 3 that treatment of methylglyoxal had no toxic effect on the functions of liver, kidney and heart and hemopoietic organs of the rats. This is indicated by the fact that the values of the respective marker enzymes and metabolites and cells remained unaltered in both control and treated groups of animals.

It is also to be noted that with the exception of alkaline phosphatase and aspartate transaminase the values of different metabolites and marker enzymes measured from the blood/serum of rat were in the range that are usually found in human samples. We checked the serum alkaline phosphatase and aspartate transaminase level in human serum by the same procedure and found that the level of these enzymes in human samples is in the range that is found in normal human serum. These are for alkaline phosphatase and aspartate transaminase 9.4 and 26 units respectively.

In experiments with dogs, during and after the treatment (90 days), no death occurred, and the animals appeared perfectly healthy and normal. However, subcutaneous injections appeared to be painful. The biochemical tests and some hematological studies were performed with blood of the animals, the results of which are presented in the Tables.

TABLE 6

Pharmacokinetic parameters of methylglyoxal in blood of mice dosed orally by 100 mg/kg body wt./day of methylglyoxal

| Time after last dose (h) | V (L/kg) | k (h − 1) | t½ (h) | CL (L/h · kg) |
|---|---|---|---|---|
| Up to 48 | 73.90 | 0.0017 | 408 | 0.125 |
| 48-120 | 50.89 | 0.0231 | 30 | 1.175 |

Abbreviations and symbols are similar to table 5.

Experimental data from 105 mice are shown in Table 7.

TABLE 7

Increase in life span of EAC cell-inoculated mice treated with methylglyoxal ascorbic acid and creatine

| Treatment group | Median survival time (days) | 60 day survivors/ 15 animals | ILS value (%) |
|---|---|---|---|
| Control | 19 | Nil | 0 |
| MG (100 mg) | Indefinite | 10 | Cure |
| MG (50 mg) + AA (50 mg) | Indefinite | 11 | Cure |
| MG (30 mg) | 26 | 1 | 34 |
| MG (30 mg) + AA (50 mg) | 32 | 3 | 65 |
| MG (30 mg) + AA (50 mg) + Cr (150 mg) | Indefinite | 13 | Cure |
| MG (30 mg) + AA (50 mg) + Cr$^a$ (150 mg) | Indefinite | 13 | Cure |

MG—Methylglyoxal; AA—Ascorbic acid, Cr—Creatine
$^a$Creatine was dissolved in water and the mice were fed instead of injected.

For this experiment and the results reported in Table 7, from a total number of 105 mice, 15 animals received a particular mode of treatment. Control group received only normal saline; the other five groups received methylglyoxal alone or methylglyoxal plus ascorbic acid or methylglyoxal plus ascorbic acid plus creatine. All the test substance was dissolved in 0.9% NaCl and 0.5 ml was separately injected intraperitoneally once day for consecutive 14 days. The day on which 105 EAC cells were inoculated into each mouse was considered as day 0. The treatment started from day 3. The amount of each compound indicated in the parentheses is the amount administered per kg body weight per day. MG—Methylglyoxal; AA—Ascorbic acid, Cr—Creatinine. a Creatine was dissolved in water and the mice were fed instead of injected.

The apparent volume of distribution (V) relates to the amount of drug in the body to the concentration of the drug (C) in the blood. The apparent volume of distribution was calculated from Cp obtained by extrapolation to t=0 (V=dose/Cp 0) considering the body as a single homogeneous compartment, i.e. in one-compartment model.

Clearance or elimination of drug from this compartment occurs in a first order fashion, the amount of drug eliminated per unit time depends on the amount (concentration) of the drug in the body compartment. Then, C=(dose/V) I exp (_kt) where k is the rate constant for elimination of the drug from the compartment. This rate constant is inversely related to the half-life of the drug (k=0.693/t½).

Pharmacokinetic evaluations—a single dose study was performed as follows. Blood methylglyoxal concentrations after single doses of 50, 100 and 200 mg/kg peaked at 4 h and came to near basal level at 8-10 h (FIG. 2). The basal level of methylglyoxal was determined from the blood of untreated mice and was found out to be around 13.7 T 2.94 nmol/ml. The individual concentration vs. time curve suggests that absorption and distribution were ongoing processes.

Different pharmacokinetic parameters were determined after a single oral dose of methylglyoxal and are presented in Table 5. It appears from the table that, for all the three doses, 50-55 min after administration of the drug its level began to increase from the basal level (lag time). The maximum concentration of methylglyoxal in blood (Cmax) after oral administration of methylglyoxal increased from 13.9 to 18.7 nmol/ml when the dose was increased from 50 mg to 100 mg respectively. However, there was a very little increase in Cmax with a dose of 200 mg as compared to that of 100 mg. The values of Cmax and other parameters based on this were calculated by subtracting the normal level of methylglyoxal, which was found out to be 13.7 T 2.94 nmol/ml. The time to reach Cmax (tmax) was found out to be 4 h. Because these results suggest that similar blood concentrations may be observed with daily doses of either 100 or 200 mg, 100 mg was chosen as the dose level for the multiple dose study. Because the concentration of methylglyoxal in the blood began to rise approximately about 1 h after administration and reached a peak at 4 h, the rate of absorption (ka) for methylglyoxal was measured from 1 to 4 h after administration of the drug.

TABLE 8

Increase in the percentage of body weight of the EAC cell inoculated mice receiving different treatments

| Treatment | Percent increase in body weight | | | | |
|---|---|---|---|---|---|
| | Day 15 | Day 20 | Day 25 | Day 30 | Day 35 |
| Control (no treatment) | 18.3 ± 1.7 | 36.6 ± 3.9[a] | — | — | — |
| MG (100) | 8.0 ± 0.7 | 10.0 ± 1.2 | 11.0 ± 1.0 | 11.2 ± 0.9 | 11.2 ± 1.1 |
| MG (50) + AA (50) | 7.5 ± 0.7 | 9.5 ± 0.8 | 10.4 ± 1.0 | 10.6 ± 0.8 | 11.0 ± 1.0 |
| MG (30) | 15.8 ± 1.3 | 19.0 ± 1.6 | 30.0 ± 2.9 | 32.9 ± 3.0 | 38.8 ± 3.0[b] |
| MG (30) + AA (50) | 11.0 ± 1.0 | 16.4 ± 1.2 | 18.3 ± 1.3 | 24.7 ± 1.9 | 30.2 ± 2.8[c] |
| MG (30) + AA (50) + Cr (150) | 9.0 ± 0.8 | 11.0 ± 1.0 | 11.5 ± 1.0 | 11.7 ± 1.2 | 11.9 ± 0.9 |

For this experiment, from a total number of 36 animals, 6 animals received a particular mode of treatment. The details of the inoculation and treatment schedule were identical to table 7. The body weight was measured from day 15. The amount of each compound indicated in the table is mg per kg body weight per day. MG—Methylglyoxal, AA—Ascorbic acid, Cr—Creatine,
[a]2 animals survived out of 6,
[b]2 animals survived out of 6,
[c]3 animals survived out of 6.

The semi-logarithmic plot (figure not presented) of methylglyoxal concentration in blood versus time appears to indicate that methylglyoxal is eliminated from a single compartment by a first order process with a half life (t½) of 2.1 to 3.6 h of three different doses. The clearance (CL) for the drug for one compartment model is CL=k I V. The elimination rate constant (k) of methylglyoxal in blood was measured 4-8 h after administration of the drug. This is because the concentration of methylglyoxal in blood reach the maximum (tmax) at 4 h after administration and came to the basal level at about 8 h. So the elimination rate constant (k) was determined by measuring methylglyoxal concentration in blood from 4-8 h after its administration.

Similar experiments of single dose study were also done with rats, and the results were similar to the study of the mice (data not presented).

Repeat dose study: In repeat dose study, the peak concentration of methylglyoxal was achieved from day three and remained at that concentration up to day 32 (FIG. 3). The last dose of methylglyoxal was administered on day 30. The peak concentration of methylglyoxal was similar in both single dose and repeat dose study. From day 32, the level of methylglyoxal gradually fell and reached the basal level around day 35. Different pharmacokinetic parameters are presented in the Tables.

Treatment of cancer-bearing animals-a survival study of EAC cell-inoculated mice treated with methylglyoxal, ascorbic acid and creatine: As mentioned above, methylglyoxal had been found to possess strong antitumor activity. Szent-Györgyi and his associates and Apple and Greenberg long ago showed remarkable antiproliferative and curative effects of methylglyoxal towards cancer-bearing animals (Szent-Györgyi et al., 1967; Együd and Szent-Györgyi, 1968; Apple and Greenberg, 1967). In in vivo and in vitro studies with animals and in vitro studies with a wide variety of human post-operative malignant tissue samples, it was observed that methylglyoxal acted specifically against malignant cells and ascorbic acid significantly augmented this anticancer effect of methylglyoxal (Ray et al., 1991, 1997a, 1997b; Biswas et al., 1997). Moreover, it was observed that creatine present in cardiac cells completely protected the animal from any possible deleterious effect of methylglyoxal treatment on cardiac mitochondria (Sinha Roy et al., 2003). It was tested whether these compounds had any curative effect on mice inoculated with EAC cells. The results are presented in the accompanying Tables. It appears that at a particular dose the antiproliferative effect of methylglyoxal is augmented in presence of ascorbic acid and further improved when the mice were treated with methylglyoxal in combination with ascorbic acid and creatine. Nearly 80% of the animals treated with this combination were completely cured.

Measurement of increase in the body weight of the mice inoculated with EAC cells and receiving treatment of methylglyoxal, ascorbic acid and creatine: Measurement of the increase in body weight of the mice inoculated with EAC cells is a good (reliable) indicator of multiplication of EAC cells in the host. Table 8 represents the results of such a study. It appears from the table that similar to the effect of methylglyoxal, methylglyoxal plus ascorbic acid and methylglyoxal plus ascorbic acid plus creatine on median survival time of EAC cell-inoculated mice (Table 7), the maximum arrest of the increase in body weight was observed with treatment of methylglyoxal plus ascorbic acid plus creatine.

Tumor growth inhibition study: Investigated the relative effect of three different drug combinations on the multiplication of cells in the peritoneal cavity of mice inoculated with EAC cells was also investigated. Table 9 shows that both methylglyoxal and methylglyoxal plus ascorbic acid treatment had significant inhibitory effect on cell proliferation. Moreover, treatment of methylglyoxal plus ascorbic acid plus creatine not only completely inhibited the cell proliferation but also made the peritoneal cavity completely dry. However, both ascorbic acid and creatine individually at the concentrations mentioned in Table 7 have no effect on EAC cells inoculated mice. FIG. 4 shows the control and treated animals.

TABLE 9

Tumor growth Inhibition study

| Treatment | No. of EAC cells (in million) | | | | % of cells present in respect of the control | | | Volume of packed cells (ml) | |
|---|---|---|---|---|---|---|---|---|---|
| | Day 1 | Day 10 | Day 14 | Day 18 | Day 10 | Day 14 | Day 18 | Day 14 | Day 18 |
| Control | 3.8 ± 0.6 | 320 ± 20 | 1800 ± 300 | 3600 ± 300 | 100 | 100 | 100 | 1.9 ± 0.3 | 3.8 ± 0.1 |
| MG (100) | - Do - | d | d | d | 0 | 0 | 0 | n.d | n.d |
| MG (50) + AA (50) | - Do - | d | d | d | 0 | 0 | 0 | n.d | n.d |
| MG (30) | - Do - | 15 ± 2 | 230 ± 10 | 820 ± 30 | 5 | 13 | 23 | 0.26 ± 0.02 | 0.96 ± 0.05 |
| MG (30) + AA (50) | - Do - | 7.5 ± 1 | 98 ± 2 | 360 ± 20 | 2.4 | 5.4 | 10 | 0.12 ± 0.01 | 0.4 ± 0.03 |
| MG (30) + AA (50) + Cr (150) | - Do - | d. | d. | d. | 0 | 0 | 0 | n.d. | n.d. |

Each group consists 10 mice. Each mouse was inoculated with 105 (0.1 million) EAC cells. Treatment with three different drug combinations were started from day 3 and continued up to day 16. The day of inoculation was considered as day 0. The mode of treatment of the drugs was similar to that of table 7. The ascites fluid containing cells were quantitatively removed from the peritoneal cavity on the indicated day and cell volume and number were counted. The details of collection and counting are described in Materials and Methods. The amount of each drug as indicated in the table is mg per kg body weight per day.
d—Dry; n.d.—Not detectable; MG—Methylglyoxal; AA—Ascorbic acid, Cr—Creatine The possible toxic effect of methylglyoxal in in vivo studies with four different species of animals was assessed. We administered creatine and/or ascorbic acid along with methylglyoxal in some toxicity studies, and the results were found to be similar where only methylglyoxal was administered. Both ascorbic and creatine are naturally occurring compounds, and their consumption had been found to have no major adverse effects on humans, the results where only methylglyoxal was administered. We also present the results of the assessment of the efficacy of methylglyoxal in combination with ascorbic acid and/or creatine to treat cancer-bearing mice is also given.

It appears from the results of acute toxicity studies with mice and rats that methylglyoxal is well tolerated. Three different modes of treatment were used, and the amounts of methylglyoxal administered were many times higher than the intended dose for treatment of cancer patients through the respective routes. The intended dose for the treatment of cancer patients had been worked out from the previous studies of Együd and Szent-Györgyi (1968) and of Apple and Greenberg (1967, 1968) and our studies presented in this paper (Tables 7-9). Acute toxicity studies with rats also provided similar results as that of the experiments with mice.

Long-term toxicity studies with four different species of animals had been investigated. For mice and rabbits, gross physical and behavioral conditions had been noted. Whereas for rats and dogs, in addition to these observations, several biochemical parameters, which are indicative of the functions of specific organs such as liver, kidney and heart, had been assessed. Additionally, histological studies with several organs of mice, which were orally treated with methylglyoxal, have indicated the respective organs that were apparently devoid of any toxic effect.

It appears from the results presented in Tables 2-4 that, similar to the acute toxicity studies with mice, the long term treatment of mice, rats, rabbits and dogs with methylglyoxal had apparently no toxic effect on the gross physical and behavioral conditions of the animals.

The fertility and teratogenicity studies with rats, as presented in this paper, have also indicated that methylglyoxal has no apparent adverse effects on the reproductive organs of the animals and also on the fetus. In a previous classic experiment, it had also been observed that methylglyoxal-treated mice were indefinite survivors and produced healthy litters.

We had also tested the long-term effect of methylglyoxal on several metabolites and marker enzymes in the blood (and serum) of rats and dogs (Tables 5 and 6). It had been observed that methylglyoxal treatment had no effect on these metabolites and enzymes. The hemoglobin content of the blood of rats remained unchanged. Methylglyoxal also had no effect on blood glucose and serum urea and creatine level, indicating no damage of pancreatic cells, and kidney functions were apparently normal. Although it had been reported that in diabetic patients the level of methylglyoxal in blood is higher in comparison to the normal subjects, our study indicates that methylglyoxal does not elevate the blood glucose level. Methylglyoxal treatment had also apparently no effect on marker enzymes of hepatic and cardiac functions. The studies with the dog and the bitch had also yielded similar results (Table 6). It is pertinent to mention here that other investigators had observed methylglyoxal pretreatment through oral route provided dose-dependent protection of gastric mucosa against different necrotizing agents—ethanol, sodium chloride and sodium hydroxide.

In the pharmacokinetic study of methylglyoxal in mice, it had been observed that the compound is appropriately cleared from the system. Moreover, the different parameters that had been worked out from this study can be gainfully utilized in its future human application.

Taken together, these results suggest the possibility of safe administration of methylglyoxal to mammals and administration to cancer patients may also be safe. Our studies presented here and in several in vivo studies by other investigators suggest that a thorough study is required to ascertain whether these deleterious effects do indeed occur in vivo and what are the consequences in intact organisms. In the absence of such study, the present authors feel it will be unwise not to make use of the potentially beneficial effects of methylglyoxal.

It appears that the anticancer effect of methylglyoxal had not been utilized and not even extensively tested. Considering this aspect and also the possible beneficial effect of ascorbic acid and creatine, both in augmenting the anticancer effect of methylglyoxal and protecting the host from any adverse effect, we have tested the efficacy of methylglyoxal in combination with ascorbic acid and creatine. The results presented in Tables 7-9 clearly indicate that the anticancer effect of methylglyoxal is significantly augmented in the presence of both ascorbic acid and creatine. A possible explanation for the augmenting effect of ascorbic acid may be provided through its role in the formation of protein aldehyde adduct. However, there is report in the literature of increased turnover of creatine phosphate in macrophages during phagocytosis, which replenishes the ATP consumed. The creatine provided to the cancer-bearing animals, along with methylglyoxal and ascorbic acid, may help in augmenting their pool of creatine phosphate in macrophages that is necessary for the phagocytosis of the malignant cells.

The results presented in this and several other previous publications strongly demand that methylglyoxal alone or in combination with other substances should be tested for the treatment of cancer patients. All the drugs now being used for the treatment of cancer patients are moderate to highly toxic, and their efficacy to arrest growth or to kill malignant cells are often doubtful. The efficacy of a particular drug, and also its mode of treatment, should be assessed by balancing the benefits and adverse effects. Moreover, without applying mere in vitro experiments and in vivo studies with animals to cancer patients, the efficacy of methylglyoxal cannot be assessed. In fact, a pilot study with methylglyoxal-based formulation on cancer patients had already been done, and the results are promising.

Figure 5:
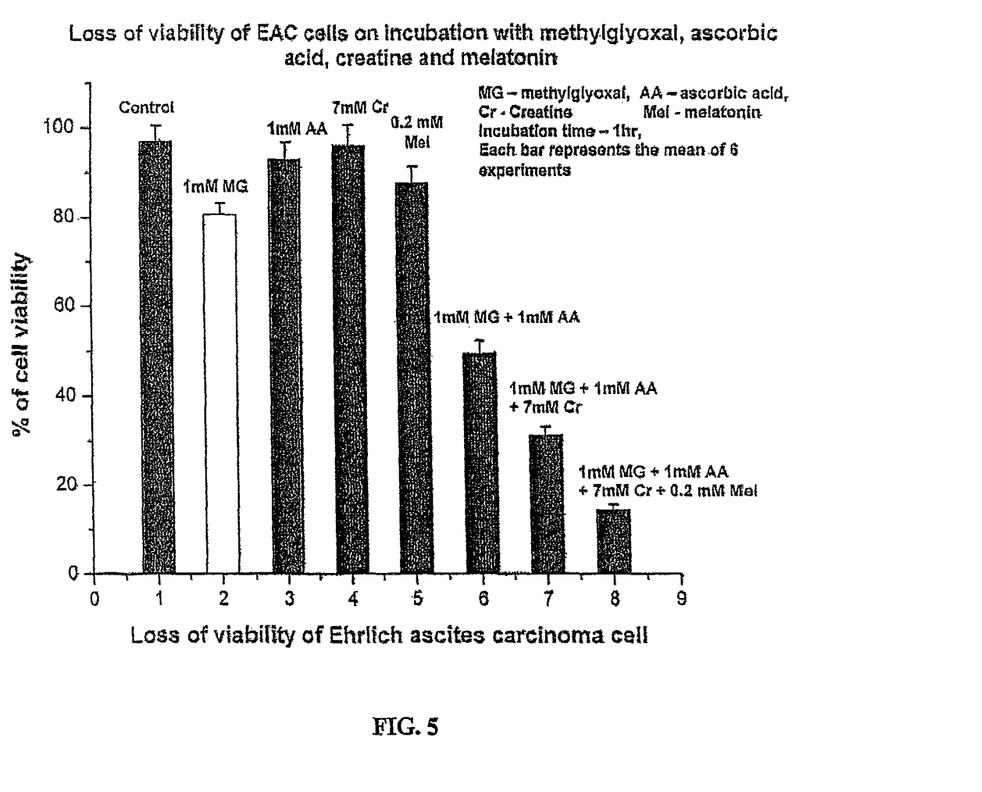
FIG. 5 is a bar graph showing the loss of viability of EAC cells on incubation with methylglyoxal, ascorbic acid, creatine and melatonin.

An additional experiment was conducted to show the loss of viability of Ehrlich ascites cells when incubated with different combinations of Methylglyoxal at a concentration of 1 mM plus 1 mM ascorbic acid showed 55% inhibitory effect on tumor cell viability, but the inhibition was almost 65% by 7 mM creatine in combination with 1 mM methylglyoxal plus 1 mM ascorbic acid. Inhibition on tumor cell viability was further increased to more than 85% by 0.1 mM melatonin with the above combination. However, melatonin alone at a concentration of 0.2 mM had been found to reduce the viability of Ehrlich ascites cells by about 10%. The results of this experiment are illustrated in FIG. 5.

A similar inhibitory effect on respiration of tumor cells was observed with the above formulation.

In Vivo Toxicity Study on Animals:

Ehrlich ascites carcinoma bearing mice were treated intraperitonially with different drug combinations in normal saline to observe their effect on body weight (table 10) and life span (table 11). Mice in the control group were similarly treated intraperitonially only with normal saline.

TABLE 10

Increase in the percentage of body weight of the EAC cell inoculated mice receiving different treatments

| Treatment | Percent increase in body weight | | | | |
|---|---|---|---|---|---|
| (/kg body weight/day) | Day 15 | Day 20 | Day 25 | Day 30 | Day 35 |
| Control (no treatment) | 18.3 ± 1.7 | 36.6 ± 3.9$^a$ | — | — | — |
| MG (100 mg) | 8.0 ± 0.7 | 10.0 ± 1.2 | 11.0 ± 1.0 | 11.2 ± 0.9 | 11.2 ± 1.1 |
| MG (50 mg) + AA (50 mg) | 7.5 ± 0.7 | 9.5 ± 0.8 | 10.4 ± 1.0 | 10.6 ± 0.8 | 11.0 ± 1.0 |
| MG (30 mg) | 15.8 ± 1.3 | 19.0 ± 1.6 | 30.0 ± 2.9 | 32.9 ± 3.0 | 38.8 ± 3.0$^b$ |
| MG (30 mg) + AA (50 mg) | 11.0 ± 1.0 | 16.4 ± 1.2 | 18.3 ± 1.3 | 24.7 ± 1.9 | 30.2 ± 2.8$^c$ |
| MG (30 mg) + AA (50 mg) + Cr (150 mg) | 9.0 ± 0.8 | 10.0 ± 0.9 | 10.5 ± 1.0 | 11.2 ± 1.1 | 11.5 ± 0.9 |
| MG (30 mg) + AA (50 mg) + Cr (150 mg) + Melatonin (0.3 mg) | 6.3 ± 0.9 | 6.9 ± 1.1 | 10.4 ± 1.0 | 10.2 ± 1.1 | 10.1 ± 1.0 |

Table 11

TABLE 11

Increase in life span of EAC cell-inoculated mice treated with methylglyoxal, ascorbic acid, creatine and melatonin

| Treatment group (/kg body weight/day) | Median survival time (days) | 60 day survivors/ 15 animals | ILS value (%) (Median survival time of (Treated/Control − 1) × 100] |
|---|---|---|---|
| Control | 20 | Nil | 0 |
| MG (100 mg) | Indefinite | 11 | Cure |
| MG (50 mg) + AA (50 mg) | Indefinite | 12 | Cure |
| MG (30 mg) | 27 | 1 | 35 |
| MG (30 mg) + AA (50 mg) | 34 | 4 | 70 |
| MG (30 mg) + AA (50 mg) + Cr$^a$ (150 mg) | Indefinite | 13 | Cure |
| MG (20 mg) + AA (50 mg) + Cr$^a$ (150 mg) | Indefinite | 11 | Cure |
| MG (20 mg) + AA (50 mg) + Cr$^a$ (150 mg) + Melatonin$^a$ (0.3 mg) | Indefinite | 14 | Cure |

The day on which $10^5$ EAC cells were inoculated into each mouse was considered as day 0. The treatment started from day 3. The test compounds, dissolved in 0.9% NaCl and 0.25 ml was separately injected intraperitonially once a day for consecutive 14 days. 6 animals received a particular mode of treatment. Control group received only normal saline. MG—Methylglyoxal, AA—Ascorbic acid, Cr—Creatine. Mice were fed with creatine and melatonin dissolved in water a—2 animals survived out of 6, b—2 animals survived out of 6, c—3 animals survived out of 6. Each set of experiment was repeated 4 times.

The day on which $10^5$ EAC cells were inoculated into each mouse was considered as day 0. The treatment started from day 3. The test compounds, dissolved in normal saline and 0.25 ml were separately injected intraperitonially once a day for 14 consecutive days. 15 animals received a particular mode of treatment. Control group received only normal saline. MG—Methylglyoxal; AA—Ascorbic acid, Cr—Creatine. a—Mice were fed with creatine and melatonin dissolved in water. Each set of experiment was repeated 4 times. The Anticancer formulation based on Methylglyoxal, in combination with ascorbic acid, creatine and melatonin is more effective for therapeutic treatment of cancer.

The invention claimed is:

1. A composition for the treatment of Ehrlich's ascites carcinoma (EAC) cancer, comprising: an oral formulation comprising 20 mg to 1 g of methylglyoxal per kg body weight per day, 50 mg of ascorbic acid per kg body weight in 3 to 6 divided doses per day 100 mg to 200 mg of creatine per kg body weight in 1 to 4 divided doses per day and 0.1 mg to 0.3 mg of melatonin in an adult per day.

2. The composition as claimed in claim 1, further comprising at least one pharmaceutically acceptable excipient.

3. The composition as claimed in claim 1, wherein melatonin is present in an amount of 0.3 mg in an adult per day oral dosage form.

4. A composition for the treatment of Ehrlich's ascites carcinoma (EAC) cancer, comprising: an oral formulation comprising 20 mg of methylglyoxal per kg body weight per day, 50 mg of ascorbic acid per kg body weight in an adult in 3 to 6 divided doses per day, 150 mg of creatine per kg body weight in 1 to 4 divided doses per day and 0.3 mg of melatonin in an adult per day.

5. The composition as claimed in claim 4, further comprising at least one pharmaceutically acceptable excipient.

6. A method of treating Ehrlich's ascites carcinoma (EAC) cancer comprising:
    administering orally to an adult patient in need of treatment 20 mg to 1 g of methylglyoxal per kg body weight per day, 50 mg of ascorbic acid per kg body weight in 3 to 6 divided doses per day, 100 mg to 200 mg of creatine per kg body weight in 1 to 4 divided doses per day and 0.1 mg to 0.3 mg of melatonin per day, or
    administering orally to an adult patient in need of treatment 20 mg of methylglyoxal per kg body weight per day, 50 mg of ascorbic acid per kg body weight in an adult in 3 to 6 divided doses per day, 150 mg of creatine per kg body weight in 1 to 4 divided doses per day and 0.3 mg of melatonin per day.

7. The method according to claim 6 wherein creatine, ascorbic acid, melatonin and methylglyoxal are administered in combination without toxic effect.

8. The method according to claim 6, wherein the method comprises administering 20 mg to 1 g of methylglyoxal per kg body weight per day, 50 mg of ascorbic acid per kg body weight in 3 to 6 divided doses per day, 100 mg to 200 mg of creatine per kg body weight in 1 to 4 divided doses per day and 0.1 mg to 0.3 mg of melatonin in an adult per day.

9. The method according to claim 6, wherein the method comprises administering 20 mg of methylglyoxal per kg body weight per day, 50 mg of ascorbic acid per kg body weight in an adult in 3 to 6 divided doses per day, 150 mg of creatine per kg body weight in 1 to 4 divided doses per day and 0.3 mg of melatonin in an adult per day.

* * * * *

UNITED STATES PATENT AND TRADEMARK OFFICE
CERTIFICATE OF CORRECTION

PATENT NO. : 9,198,896 B2
APPLICATION NO. : 12/858708
DATED : December 1, 2015
INVENTOR(S) : Manju Ray

It is certified that error appears in the above-identified patent and that said Letters Patent is hereby corrected as shown below:

Title Page of the Patent, Column 2, OTHER PUBLICATIONS, Line 14, delete "Ehlich" and insert -- Ehrlich --

Claims

Column 21, Line 29, Claim 1, delete "day 100 mg" and insert -- day, 100 mg --

Signed and Sealed this
Thirty-first Day of May, 2016

Michelle K. Lee
*Director of the United States Patent and Trademark Office*